United States Patent [19]

Zettlmeissl et al.

[11] Patent Number: 5,618,713
[45] Date of Patent: Apr. 8, 1997

[54] MUTANTS OF HUMAN ANTITHROMBIN III

[75] Inventors: Gerd Zettlmeissl, Lahntal; Hermann E. Karges, Marburg; Achim Becker, Dautphetal, all of Germany

[73] Assignee: Behringwerke Aktiengesellschaft, Marburg, Germany

[21] Appl. No.: 993,910

[22] Filed: Dec. 18, 1992

Related U.S. Application Data

[63] Continuation of Ser. No. 469,913, Jan. 22, 1990, abandoned.

[30] Foreign Application Priority Data

Jan. 24, 1989 [DE] Germany .......................... 39 01 917.9

[51] Int. Cl.$^6$ .............................. C12N 9/64; A61K 38/17
[52] U.S. Cl. .............................. 435/226; 514/12; 530/350
[58] Field of Search ..................................... 530/380, 387, 530/350; 435/69.6, 226; 514/12

[56] References Cited

U.S. PATENT DOCUMENTS 4,632,981 12/1986 Bock et al. .............................. 530/393

FOREIGN PATENT DOCUMENTS

0090502A2 10/1983 European Pat. Off. .

OTHER PUBLICATIONS

"Chromogene Substratmethoden zur Antithrombin III–Bestimmung", J. Schrader et al., (1986), Das Arztliche Laboratorium, pp. 111–114.

Zettlmeissl et al., "Influence of Glycosylation on the Functional Properties of Human Therapeutic Plasma Proteins", Protein Glycosylation: Cellular, Biotechnological and Analytical Aspects, GBF Monographs, vol. 15 (ed. H.5. Conradt), pp. 259–268, 1991.

Bowie et al., "Deciphering the Message in Protein Sequences: Tolerance to Amino Acid Substitutions", Science, vol. 247, pp. 1306–1310, Mar. 1990.

G. Zettlemeissl et al., "Expression of Biologically Active Human Anti–thrombin III in Chinese Hamster Ovary Cells," Bio/Technology, vol. 5, pp. 720–725 (Jul. 1987).

M. Hoylaerts et al., "Involvement of Heparin Chain Length in the Heparin–catalyzed Inhibition of Thrombin by Antithrombin III," J. Biol. Chem, vol. 259, No. 9, pp. 5670–5677 (May 1984).

C. Peterson et al., "Isolation and Characterization of an Antithrombin III Variant with Reduced Carbohydrate Content and Enhanced Heparin Binding," J. Biol. Chem., vol. 260, No. 1, pp. 610–615 (Jan. 1985).

S. Brennan et al. "Physiological Variant of Antithrombin–III Lacks Carbohydrate Sidechain at Asn 135," FEBS Letters, vol. 219, No. 2, pp. 431–436 (Jul. 1987).

Yasushi Morinaga et al., "Improvement of Oligonucleotide–Directed Site–Specific Mutagenesis Using Double–Stranded Plasmid DNA," Bio/Technology, pp. 636–639 (Jul. 1984).

W. Kramer et al., "The Gapped Duplex DNA Approach to Oligonucleotide–Directed Mutation Construction," Nucl. Acids Res., vol. 12, No. 24, pp. 9441–9456 (1984).

G. Zettlmeissl et al., "Efficient Expression System for Human Antithrombin III in Baby Hamster Kidney Cells," Behring Inst. Mitt., No. 82, pp. 26–34 (1988).

F. Sanger et al., "DNA Sequencing with Chain–Terminating Inhibitors," Proc. Natl. Acad. Sci. USA, vol. 74, No. 12, pp. 5463–5467. (1977).

A. Hensen et al., "III. Antithrombin III Assay," Thromb. Diatl. Haemorrh., vol. 9, pp. 18–29 (1963).

J. Schrader et al., "Methoden zur Bestimmung des Antithrombin III (Methods for the Determination of Antithrombin III)", Arztl. Lab., vol. 29, pp. 35–39, (1983).

S. Engelbrecht et al., "Separation of Human Leucocyte Enzymes Alanine Aminopeptidase, Cathepsin G, Collagenase, Elastase and Myeloperoxidase," Hoppe–Seyler's Z. Physiol. Chem., vol. 363, pp. 305–315, (Mar. 1982).

K. Nakajima et al., "Mapping the Extended Substrate Binding Site of Cathepsin G and Human Leukocyte Elastase," J. Biol. Chem., vol. 254, No. 10, pp. 4027–4031 (May 1979).

Jorgensen et al. *Biochem J.* 231:59–63 (1985).

Molho–Sabatier et al. *J Clin Invest* 84:1236–1242 (1989).

*Primary Examiner*—Charles L. Patterson, Jr.
*Attorney, Agent, or Firm*—Finnegan, Henderson, Farabow, Garrett & Dunner, L.L.P.

[57] ABSTRACT

Mutants of AT III which have been advantageously modified at one or more potential glycosylation sites or at the Arg393 position are described. As a rule, combination of the mutations enhances the advantageous modifications.

4 Claims, No Drawings

MUTANTS OF HUMAN ANTITHROMBIN III

This application is a continuation of application Ser. No. 07/469,913, filed Jan. 22, 1990, now abandoned.

The invention relates to mutants of AT III which have improved properties by comparison with wild-type AT III. Modification at one or more potential glycosylation sites (for example Asn 135, Asn 155) increases the heparin-binding/heparin-activating properties while retaining the protease specificity of AT III. Alterations at the position Arg 393 result in alterations in the specificity towards proteases. As a rule, combination of the mutations enhances the improvements.

The cDNA coding for human antithrombin III (AT III) and the expression thereof in E. coli are described in European Patent Application EP 0 090 505 A2. Expression of AT III is additionally shown in recombinant yeasts (EP 0 256 302A2) and mammalian cells (DE 3 624 453 A1). It emerged from these experiments that only AT III secreted by mammalian cells into the culture medium shows complete biological activity in vitro and has a complex carbohydrate structure very similar to the plasma protein (Zettlmeissl et al., BioTechnology, 1987, 5, 720–725).

The molecular weight of about 58 kd of recombinant AT III from mammalian cells corresponds to that of the protein purified from plasma. The amino acid sequence of mature human AT III is depicted in Tab. 1.

AT III is a member of the serpin family of proteins and accordingly has great homology to protease inhibitors such as alpha-1 antitrypsin, alpha-2 antiplasmin, heparin cofactor II, alpha-1 antichymotrypsin, plasminogen activator inhibitor etc. When the serine protease thrombin interacts with AT III it cleaves the Arg393-Ser394 bond and there is formation of a covalent AT III-thrombin complex. Thrombin loses its protease activity on complexation. In the absence of heparin, AT III is a relatively poor inhibitor of thrombin. Optimal concentrations of heparin increase the rate constant of the AT III-thrombin association reaction by a factor of at least 2000 (Hoylaerts et al., J. Biol. Chem., 1984, 259, 5670–5677). Two forms of AT III (alpha and beta) exist in human plasma and have different affinities for heparin (Peterson and Blackburn, J. Biol. Chem., 1985, 260, 610–615; Brennan et al., FEBS LETT., 1987, 219, 431–436). Whereas AT IIIalpha, which occurs to the extent of 90–95% in plasma, has carbohydrate side-chains on the Asn residues 96, 135, 155 and 192, in AT IIIbeta only the positions 96, 155 and 192 are occupied. The physiological role of the two AT III forms is unknown.

The technique of directed mutagenesis permits the introduction of specific alterations into the AT III cDNA which lead to modifications in the amino acid composition of AT III. Methods for directed mutagenesis which use single-stranded DNA or heteroduplex DNA have been disclosed (Morinaga et al., BioTechnology, 1984, 7, 636–639; Kramer et al., Nucl. Acid Res., 198, 12, 9441–9456). Tab. 2 shows, by way of example, some oligonucleotides which have been employed for the directed mutagenesis of human AT III.

Mutants which have at one or more of the glycosylation sites Asn 96, Asn 135, Asn 155 and Asn 192 a different amino acid, preferably Gln, have now been prepared, which improves the heparin-binding/heparin-activating properties while retaining the protease specificity; in addition, mutants which have been modified at positionArg393 (preferably mutation to Met or Val) have been prepared, which brings about a modification of enzyme specificity.

Mutants with improved heparin-binding/heparin-activating properties have advantages in AT III/heparin combination therapy because it is possible, where appropriate, to use lower heparin doses for the therapy.

On the other hand, specificity mutants result in new molecules in which the AT III property of possible heparin activation can be transferred to mutated molecules having affinity to new proteases (for example elastase, plasmin etc.), so that molecules of this type make it possible for therapy policies robe altered in an advantageous manner by reason of altered dosages.

Mutated AT III proteins can be expressed in mamalian cells, purified by standard methods and examined for their protease specificity or their heparin-activating properties, their biochemical/biophysical properties and/or their clinical parameters. The synthesis of modified forms of AT III is achieved by a vector/host cell system which rapidly leads to high expression rates (Zettlmeissl et al. (1988) Behring Inst. Mitt. 82, 26–34).

Accordingly, the invention relates to AT III mutants which (1) have at one or more of the glycosylation sites Asn 96, Asn 135, Asn 155 and Asn 192 a different amino acid, preferably Gln, (2) are modified at position Arg 393 (preferably mutation to Met or Val), (3) have a combination of mutations (1) and (2) which, as a rule, enhance the improvements.

The invention is furthermore described in the examples and in the patent claims.

EXAMPLE 1

Synthesis of AT III mutants (general method)

A 1.4 kb fragment which contains the entire coding region of human AT III cDNA was isolated from the plasmid pbetaAT6 (EP 0 256 302 A2) by digestion with EcoRI/HindIII. This fragment was cloned into the polylinker (cleaved with EcoRI/HindIII) of the mutagenesis vector pMA 5–8. The resulting plasmid was called pMAATIII.

After the mutagenesis had been carried out (see description under "Mutagenesis"), the mutated cDNA was isolated by cutting with SacII/XbaI and cloned into the expression vector pAB 3-1 (AT III wild-type) which had likewise been digested with SacII/XbaI, which resulted in the plasmid pABmut. The pABmut plasmids carry the SV40 early enhancer/promoter unit, the SV40 polyadenylation site for early transcripts and the CMV immediate early enhancer (Zettlmeissl et al. loc. cit. ) in addition to the particular mutated cDNA.

The pABmut plasmids were purified on CsCl gradients and cotransfected with with plasmids pSV2dhfr and pRMH140 in BHK cells (ATCC CCL10) as described by Zettlmeissl et al., loc. cit. The resistant clones (about 40–100) emerging after dual selection in DME medium+ 10% FCS+400 µg/ml G418 and 1 µM methotrexate (standard growth medium) were combined as clone mixture in T25 culture vessels. The mixed clones were expanded via T80 and T180 culture vessels in standard growth medium to plastic roller bottles (1750 cm$^2$) and cultured adherent therein to confluence. The confluent cells were washed twice with 200 ml of Iscove's medium (Behringwerke AG, Marburg) (for 2 hours at 37° C. in each case) and subsequently rolled with 500 ml of the same medium as harvest medium for 48 hours. The harvest medium was separated from cellular constituents by centrifugation. Aliquots of the conditioned harvest media were examined for their AT III antigen content in an ELISA specific for human AT III (Zettlmeissl et al. 1987, BioTechnology 5, 720–725). The levels of expression for wild-type AT III (AT III-WT) and various mutants measured in this way are shown by way of example in Tab. 3.

AT III-WT and mutated proteins derived therefrom were purified from the harvest media by a standard method (affinity chromatography using heparin-Sepharose, followed by fractional ammonium sulfate precipitation) (zettlmeissl et al. 1987) and subsequently characterized.

Mutant AT III molecules can also be expressed using other expression vectors in various permanent mammalian cell lines in accordance with the state of the art.

EXAMPLE 2

Mutagenesis/ general method (Kramer et al., Nucl. Acids Res. (1984) 12, 9441–9456) Single-stranded DNA of the mutagenesis vector pMAATIII which had been transformed in the *E. coli* strain WK6 was isolated by standard methods.

Plasmid DNA of pMCS-8 was cut with EcoRI/HindIII, and the vector fragment (3.8kb) was purified from an agarose gel by paper elution (Maniatis. et al. 1982, Molecular Cloning—A Laboratory Manual, Cold Spring Harbor, N.Y.).

To prepare a gapped duplex DNA, 0.1 pmol of double-stranded fragment (from pMC) and 0.5 pmol of single-stranded DNA (pMAATIII) were heated in 12.5 mM Tris-HCl pH 7.5+190 mM KCl (final volume 40 µl) at 100° C. for 4 minutes and subsequently incubated at 65° C. for 10 minutes. To hybridize on the mutagenesis oligonucleotide (see Tab. 2) 8 µl of the said hybridization solution were heated with 4–8 pmol (2 µl) of the enzymatically phosphorylated oligonucleotide at 65° C. for 5minutes and then slowly cooled to room temperature. Addition of 24 µl of $H_2O$, 4 µl of 10× fill-in buffer (625 mM KCl, 275 mM Tris-HCl pH 7.5, 150mM $MgCl_2$, 20 mM DTT, 0.5 mM ATP and 0.25 mM of each of the four dNTPs), 1 µl of T4 DNA ligase (5 U/µl) and 1 µl of Klenow fragment of DNA polymerase I (1U/µl) was followed by incubation at room temperature for 45 minutes. 5 µl of filled-in gapped duplex DNA were transformed into WK6 muts (mutS215:Tn10). The entire transformation mixture is grown in a shake culture in LB medium+25 µg/ml chloramphenicol (10 ml) at 37° C. overnight. The plasmid DNA was purified from the entire mixture by standard methods (Maniatis et al. 1982). About 20 ng of the purified plasmid were transformed into WK6. The transformants were selected on LB plates containing 25 µg/ml chloramphenicol.

Five of these transformants were analyzed for the desired mutation by a suitable sequence reaction (C-, T-, A- or G-specific). Positive clones were verified by detailed sequence analysis in the region of the mutagenesis site (Sanger et al. (1988), Proc. Natl. Acad. Sci. USA 74, 5463–5467).

EXAMPLE 3

AT III—Met 393: AT III—Val 393 and AT III—Leu 393

With the aim of generating a molecule with specificity similar to alpha1 antitrypsin (elastase inhibitor), Arg393 of AT III (P1 position) was converted into a Met, Val or Leu. Oligonucleotides Nos. 1, 2 and 3 from Tab. 2 were employed for the mutagenesis.

The mutants are synthesized and released into the culture medium by BHK cells in amounts comparable to AT III wildtype (WT) (Tab. 4), show a behavior towards anti-AT III sera from rabbits which is identical to AT III plasma and AT III-WT, and can be purified to purities greater than 95% by the standard method described above in analogy to AT III-WT. These mutants do not differ from AT III-WT in the binding and elution behavior on heparin-Sepharose. This indicates that the heparin-binding and heparin-activating behavior of the mutants is intact.

The mutants no longer have progressive inhibitory (Hensen et al., 1963, Thromb. Diatl. Haemorrh. 9, 18–29) or heparin cofactor activity (Schrader et al., 1986, Ärztl. Lab. 32, 111–114) towards thrombin (Tab. 3).

As taught in Hensen et al., progressive inhibiting activity is measured by an antithrombin III assay according to the principle that the material to be tested is incubated with thrombin. The rate of thrombin inactivation is measured and is used as a standard of antithrombin III activity.

In the procedure, a bovine thrombin solution of 50 N.I.H. units/ml, stored at−25° C., after being thawed is kept as melting ice; 0.2 ml of this thrombin solution with 0.6 ml veronal buffer, in a siliconized tube, is placed in a waterbath at 37° C. After a minimum of 2 minutes preheating, 0.2 ml of the material to tested (heat-defibrinated plasma or serum or a plasma fraction) is added to the mixture, and a chronometer is started. Exactly 1, 3 and 5 minutes later, 0.2 ml of this incubation mixture is added to 0.3 ml diluted bovine $BaSO_4$-plasma which has been pre-heated in the waterbath for 2–20 minutes and kept in non-siliconized tubes. The clotting times obtained are registered. The determination is made in duplicate.

If the antithrombin III activity in the sample tested is found to be low (less than 50% of the normal), then the determination should be repeated with the double quantity of the material to be tested (0.4 ml and 0.4 ml veronal buffer). On the other hand, where the findings indicate greatly increased activity the determination must be carried out again with material of higher dilution, because an antithrombin III activity exceeding 150% gives too long (poorly readable) thrombin times.

In the calculation, three times are obtained per determination. Each time is converted into its equivalent thrombin activity using a standard curve, coagulation time (seconds) vs. thrombin dilution (1/1=10 units/ml).

As taught in Schrader et al., for the determination of the heparin cofactor activity of the AT III mutants with the test kit Berichrom® (Behringwerke AG, Marburg) a solution with the particular AT III mutant was incubated with an excess of heparin and thrombin. The produced AT III mutant-heparin-complex inhibits a part of the thrombin. The non-inactivated part of the thrombin cleaves the chromogenic substrate which was added to the solution and the amount of produced p-nitroaniline was measured at 405 nm photometrically.

In contrast to AT III-WT, the three mutants inhibit leukocyte elastase. The elastase was isolated from human leukocytes by the method described by Engelbrecht et al. (Hoppe-Seyler's Ztschr. Physiol. Chemie 363, 305–315, 1982). The substrate used was the MeO-Suc-Ala-Ala-Pro-Val-pNA (Calbiochem) described by NakaJima et al. (J. Biol. Chem. 254, 4027–4032, 1979). The liberation of the paranitroaniline from the substrate was measured in a spectrophotometer as the increase in absorption at 405 nm within 15 min. This absorption was defined as 100% activity of the PMN elastase enzyme. The inhibitors were preincubated in concentrations increasing up to a maximum of 100 µg/ml with the enzyme for one hour. The enzyme reaction was then started with the substrate. The assay was carried out in 0.1 mol/l HEPES, pH 7.5, +0.1 mol/l sodium chloride. The substrate concentration was 0.13 mmol/l. The IC50 was defined as the inhibitor concentration, in µg/ml, which inhibited 50% of the. enzyme activity. Substances which showed no inhibiting action at a maximum concentration of 100 μg/ml were designated inactive. The reference inhibitor used was alphal protease inhibitor (alphal PI, alphal antitrypsin), which had an inhibition value of 3.7. AT III-WT showed no inhibition of PMN elastase activity. AT III Val showed an activity of 4.0 μg/ml, comparable to alphal PI, whereas AT III Met and AT III Leu were distinctly less active, with 28 and 65 mg/ml respectively (see Table which follows).

The described PMN elastase assay was used to determine the KI for AT III-Val 393 by comparison with alphal PI. The concentrations of the substrate McO-Suc-Ala-Ala-pro-val-pNA Val-pNA employed were 0.0011, 0.0022, 0.0044, 0.0087, 0.0175, 0.035, 0.7 mmol/1. The concentration of the inhibitor was $3.5 \times 10^{-8}$ mol/1.

In both cases the inhibition of PMN elastase is a non-competitive inhibition ( see Table which follows ). The KI values for alphal PI and AT III-Val 393 are virtually identical.

EXAMPLE 4

AT III-Gln135 and AT III-Gln155

One aim of the experiments claimed in this application as invention is to examine the effect of glycosylation in the AT III molecule on the biological and biochemical properties of AT III. Asn→Gln exchanges in positions 135 and 155 were used to generate two AT III mutants (AT III-Gln135 and AT III-Gln155) each of which lacked a carbohydrate side-chain. The mutagenesis oligonucleotides employed were oligonucleotides 8 and 9 (Tab. 2). The expression rates for both mutants in BHK cells (AT III in the culture medium) are, as shown in Tab. 4, of the same order of magnitude as for AT III-WT. Both mutants show a behavior towards anti-AT III sera from rabbits which is identical to AT III plasma and AT III-WT, with respect to specific progressive inhibitory and heparin cofactor activity (Tab. 4), and can be purified to purities greater than 95% by the standard method described above.

The two mutants were examined for their relative ability to inactivate thrombin as a function of the heparin concentration in the assay and compared with AT III plasma, AT III-WT and the mutant AT III-Lys49 (Tab. 5).

The assay was carried out under the following conditions: 0.02 U (antigen)/ml AT III (AT III plasma, AT III-WT or AT III-Mut) was preincubated with 0.3 IU/ml alpha-thrombin (human), 2 KIU/ml aprotinin (Behringwerke) and heparin (Hoffmann-LaRoche) in concentrations of 0–25 IU/ml in a volume of I ml at 37° C. for 5minutes. After addition of 100 μl of substrate reagent (2 mM HD-CHA-But-Arg-pNA), the change in extinction at 405 nm (37° C.) was followed kinetically. The maximum inhibition of alpha-thrombin at heparin saturation was set equal to 100%.

The inhibition of thrombin at low heparin concentrations by the mutants AT III-Gln135 and AT III-Gln155 is better than that of AT III plasma and AT III-WT (Tab. 5).

Tab. 5 indicates the heparin concentration at half-maximum thrombin inhibition (c ½) for AT III plasma, AT III-WT and various AT III mutants.

EXAMPLE 5

AT III-Gln135/155

The mutations described in Example 4 were combined in one AT III molecule by sequential mutagenesis with oligonucleotides 8 and 9 (Tab. 2). The mutated protein behaves like a recombinant wild-type AT III molecule in the standard purification method described.

The improved inhibition of alpha-thrombin at low heparin concentrations found with AT III-Gln135 and with AT III-Gln155 is even more pronounced in the case of AT III-Gln135/155 (Tab. 5).

TABLE 1

| 1 | HGSPVDICTA | KPRDIPMNPM | CIYRSPEKKA | TEDEGSEQKI | PEATNRRVWE |
|---|---|---|---|---|---|
| 51 | LSKANSRFAT | TFYQHLADSK | NDNDNIFLSP | LSISTAFAMT | KLGACNDTLQ |
| 101 | QLMEVFKFDT | ISEKTSDQIH | FFFAKLNCRL | YRKANKSSKL | VSANRLFGDK |
| 151 | SLTFNETYQD | ISELVYGAKL | QPLDFKENAE | QSRAAINKWV | SNKTEGRITD |
| 201 | VIPSEAINEL | TVLVLVNTIY | FKGLWKSKFS | PENTRKELFY | KADGESCSAS |
| 251 | MMYQEGKFRY | RRVAEGTQVL | ELPFKGDDIT | MVLILPKPEK | SLAKVEKELT |
| 301 | PEVLQEWLDE | LEEMMLVVHM | PRFRIEDGFS | LKEQLQDMGL | VDLFSPEKSK |
| 351 | LPGIVAEGRD | DLYVSDAFHK | AFLEVNEEGS | EAAASTAVVI | AGRSLNPNRV |
| 401 | TFKANRPFLV | FIREVPLNTI | IFMGRVANPC | VK | |

TABLE 2

Examples of mutagenesis oligonucleoides

| No. | Sequence | Mutation |
|---|---|---|
| 1 | 5' GGG GTT TAG CGA CAT GCC AGC AAT CAC 3' | Arg393-Met |
| 2 | 5' GGG GTT TAG CGA AAC GCC AGC AAT CAC 3' | Arg393-Val |
| 3 | 5' GGG GTT TAG CGA AAG GCC AGC AAT CAC 3' | Arg393-Leu |
| 4 | 5' GGG GTT TAG CGT ACG GCC AGC 3' | Ser394-Thr |
| 5 | 5' GGG GTT TAG CAT ACG GCC AGC 3' | Ser394-Met |
| 6 | 5' GGA CAG TTC CTT GAC ACG CCG G 3' | Trp49-Lys |
| 7 | 5' G GAG GGT GTC CTG ACA AGC ACC CAG C 3' | Asn96-Gln |
| 8 | 5' GGA GGA TTT CTG GGC TTT TCG | Asn135-Gln |
| 9 | 5' G GTA GGT CTC CTG GAA GGT AAG G 3' | Asn155-Gln |
| 10 | 5' CG GCC TTC GGT CTT CTG GGA CAC CC 3' | Asn192-Gln |

TABLE 3

Inhibition of elastase from human polymorphonuclear granulocytes (PMN elastase)

| Substance | IC$_{50}$ (µg/ml) | k$_I$ (mol/l) |
| --- | --- | --- |
| alpha$_1$ PI | 3.7 | 1.7 × 30$^{-8}$ |
| AT III - WT | — | n.d. |
| AT III - Met 393 | 28.0 | n.d. |
| AT III - Val 393 | 4.0 | 1 × 10$^{-8}$ |
| AT III - Leu 393 | 65.0 | n.d. |

— = no inhibition (IC$_{50}$ > 100 µg/ml)
n.d. = not determined

TABLE 4

Expression and purification of AT III mutants

| | Conc. in roller supernatants[1] (mg/l) | Purification by standard method | PI[2] (U/mg) | HC[3] (U/mg) |
| --- | --- | --- | --- | --- |
| ATIII-Plasma | — | +++ | 4–6.5* | 4–6.5* |
| ATIII-WT | 4.2 | +++ | 6.2 | 5 |
| ATIII-Met393 | 5.5 | +++ | 0 | 0 |
| ATIII-Val393 | 4.8 | +++ | 0 | 0 |
| ATIII-Leu393 | 9.8 | +++ | 0 | 0 |
| ATIII-Thr394 | 9.7 | +++ | n.d. | 3.5 |
| ATIII-Lys49 | 3.3 | ++ | 4.6 | 4.3 |
| ATIII-Gln135 | 8 | +++ | 3.9 | 4.5 |
| ATIII-Gln155 | 3.6 | +++ | 4.2 | 5.5 |
| ATIII-Gln135/155 | 1.2 | +++ | n.d. | 3.8 |

[1] 40 h serum-free supernatants (ELISA) of BHK cells
[2] progressive inhibitory activity (Hensen et al. 1963)
[3] heparin cofactor activity (Schrader et al. 1986)
n.d. = not determined
*batch-dependent range of variation

TABLE 5

Dependence of thrombin inactivation on the heparin concentration

| | c$_{½}$Heparin[1] (mIU/ml) |
| --- | --- |
| ATIII-Plasma | 65 |
| ATIII-WT | 65 |
| ATIII-Gln135 | 22 |
| ATIII-Gln155 | 22 |
| ATIII-Gln135/155 | 5 |
| ATIII-Lys49 | greater than 360 |

[1] heparin concentration at half-maximum relative thrombin inhibition

We claim:

1. An antithrombin III mutant, which contains an amino acid substitution at position 96, 135, 155, 192, or 393, wherein the substitution can be present either singly or in combination with one or more other substitutions, and wherein the amino acid substituted at position 393 is not His.

2. An antithrombin III mutant, wherein a Lys amino acid is substituted for Trp at position 49.

3. An antithrombin III mutant, as claimed in claim 1, wherein a Lys amino acid is substituted for Trp at position 49.

4. A pharmaceutical composition comprising one or more of the mutants as claimed in claims 1, 2, or 3 together with a pharmaceutically acceptable auxiliary or excipient.

* * * * *